(12) United States Patent  
Trah et al.

(10) Patent No.: US 8,410,026 B2
(45) Date of Patent: Apr. 2, 2013

(54) PYRIDAZINE FUNGICIDES

(75) Inventors: Stephan Trah, Stein (CH); Clemens Lamberth, Stein (CH); Raphael Dumeunier, Stein (CH); Sebastian Volker Wendeborn, Stein (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 0 days.

(21) Appl. No.: 12/863,377

(22) PCT Filed: Jan. 14, 2009

(86) PCT No.: PCT/EP2009/000166
§ 371 (c)(1),
(2), (4) Date: Jan. 24, 2011

(87) PCT Pub. No.: WO2009/090039
PCT Pub. Date: Jul. 23, 2009

(65) Prior Publication Data
US 2011/0112108 A1    May 12, 2011

(30) Foreign Application Priority Data

Jan. 16, 2008  (GB) .................................. 0800762.7

(51) Int. Cl.
*A01N 43/58*    (2006.01)
*A61K 31/50*    (2006.01)
*C07D 237/00*   (2006.01)
(52) U.S. Cl. ................... 504/238; 514/248; 544/224
(58) Field of Classification Search .......... 544/224; 514/248; 504/236, 238
See application file for complete search history.

(56) References Cited

FOREIGN PATENT DOCUMENTS

| EP | 1767529 A | 3/2007 |
| EP | 1775290 A | 4/2007 |
| WO | 2008009406 | 1/2008 |

OTHER PUBLICATIONS

Pinedo et al. (2000).*
McMahon et al. (2000).*

* cited by examiner

*Primary Examiner* — Paul V. Ward
(74) *Attorney, Agent, or Firm* — R. Kody Jones

(57) ABSTRACT

The present invention relates to novel pyridazine derivatives of formula (I) as active ingredients which have microbiocidal activity, in particular fungicidal activity: wherein $R^1$ is methyl, ethyl or isopropyl; $R^2$ is chloro, fluoro, hydroxy or $C_1$-$C_2$alkoxy; $R^3$ is H, chloro, fluoro, methoxy or $C_1$-$C_3$alkyl; $R^4$ is chloro, fluoro or bromo; and $R^5$ is H, fluoro or methoxy; or an agrochemically usable salt form thereof; with the proviso that when $R^1$ is methyl, $R^2$ is chloro and $R^3$ is H, then $R^4$ or $R^5$ is different from fluoro.

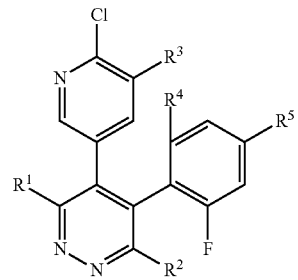

16 Claims, No Drawings

PYRIDAZINE FUNGICIDES

This application is a 371 of International Application No. PCT/EP2009/000166 filed Jan. 14, 2009, which claims priority to GB 0800762.7 filed Jan. 16, 2008, the contents of which are incorporated herein by reference.

The present invention relates to novel pyridazine derivatives as active ingredients which have microbiocidal activity, in particular fungicidal activity. The invention also relates to preparation of these active ingredients, to novel heterocyclic derivatives used as intermediates in the preparation of these active ingredients, to preparation of these novel intermediates, to agrochemical compositions which comprise at least one of the novel active ingredients, to preparation of these compositions and to use of the active ingredients or compositions in agriculture or horticulture for controlling or preventing infestation of plants, harvested food crops, seeds or non-living materials by phytopathogenic microorganisms, preferably fungi.

In addition, the present invention also relates to the use of these novel pyridazine derivatives as plant growth regulators (PGRs).

Furthermore, the present invention also relates to compositions comprising the novel pyridazine derivatives that improve plants, a process which is commonly and hereinafter referred to as "plant health".

The present invention further relates to the use of these novel pyridazine derivatives in the treatment of cancer and to fungicidal or pharmaceutical compositions comprising at least one of these compounds as active component.

The present invention provides a compound of formula I:

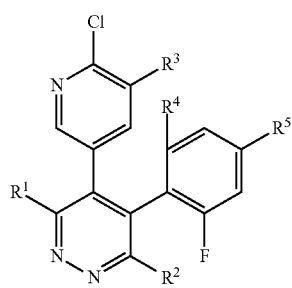

(I)

wherein
$R^1$ is methyl, ethyl or isopropyl;
$R^2$ is chloro, fluoro, hydroxy or $C_1$-$C_2$alkoxy;
$R^3$ is H, chloro, fluoro, methoxy or $C_1$-$C_3$alkyl;
$R^4$ is chloro, fluoro or bromo; and
$R^5$ is H, fluoro or methoxy;
or an agrochemically usable salt form thereof;
with the proviso that when $R^1$ is methyl, $R^2$ is chloro and $R^3$ is H, then $R^4$ or $R^5$ is different from fluoro.

The above or below mentioned pyridinyl may carry one or two identical or different substituents. Examples of substituents are: halogen, alkyl, haloalkyl, cycloalkyl, cycloalkylalkyl, alkenyl, haloalkenyl, cycloalkenyl, alkynyl, haloalkynyl, alkyloxy, haloalkyloxy, cycloalkoxy, alkenyloxy, haloalkenyloxy, alkynyloxy, haloalkenyloxy, alkylthio, haloalkylthio, cycloalkylthio, alkenylthio, alkynylthio, alkylcarbonyl, haloalkylcarbonyl, cycloalkylcarbonyl, alkenylcarbonyl, alkynylcarbonyl, alkoxyalkyl, cyano, nitro, hydroxy, mercapto, amino, alkylamino, dialkylamino. Typical examples for optionally substituted pyridin-3-yl or quinolin-2-yl include 6-chloropyridin-3-yl, 6-bromopyridin-3-yl, 6-methylpyridin-3-yl, 6-(trifluoromethyl)-pyridin-3-yl, 6-methoxypyridin-3-yl, 6-(trifluoromethoxy)-pyridin-3-yl, 5,6-dichloropyridin-3-yl, 5,6-dimethylpyridin-3-yl, quinolin-2-yl, 4-chloroquinolin-2-yl, 4-methylquinolin-2-yl, 4-methoxyquinolin-2-yl.

Halogen means fluorine, chlorine, bromine or iodine.

The above or below mentioned alkyl radicals may be straight-chained or branched.

Alkyl on its own or as part of another substituent is, depending upon the number of carbon atoms mentioned, for example, methyl, ethyl, propyl, butyl, pentyl, hexyl and the isomers thereof, for example, isopropyl, isobutyl, sec-butyl, tert-butyl, isopentyl or tert-pentyl.

A haloalkyl group may contain one or more identical or different halogen atoms and, for example, may stand for $CH_2Cl$, $CHCl_2$, $CCl_3$, $CH_2F$, $CHF_2$, $CF_3$, $CF_3CH_2$, $CH_3CF_2$, $CF_3CF_2$ or $CCl_3CCl_2$.

Cycloalkyl on its own or as part of another substituent is, depending upon the number of carbon atoms mentioned, for example, cyclopropyl, cyclobutyl, cyclopentyl or cyclohexyl.

Alkenyl on its own or as part of another substituent is, depending upon the number of carbon atoms mentioned, for example, ethenyl, allyl, 1-propenyl, buten-2-yl, buten-3-yl, penten-1-yl, penten-3-yl, hexen-1-yl or 4-methyl-3-pentenyl.

Alkynyl on its own or as part of another substituent is, depending upon the number of carbon atoms mentioned, for example, ethynyl, propyn-1-yl, propyn-2-yl, butyn-1-yl, butyn-2-yl, 1-methyl-2-butynyl, hexyn-1-yl or 1-ethyl-2-butynyl.

The presence of one or more possible asymmetric carbon atoms in a compound of formula I means that the compounds may occur in optically isomeric, that means enantiomeric or diastereomeric forms. As a result of the presence of a possible aliphatic C=C double bond, geometric isomerism, that means cis-trans or (E)-(Z) isomerism may also occur. Also atropisomers may occur as a result of restricted rotation about a single bond. Formula I is intended to include all those possible isomeric forms and mixtures thereof. The present invention intends to include all those possible isomeric forms and mixtures thereof for a compound of formula I.

In each case, the compounds of formula I according to the invention are in free form or in an agronomically usable salt form.

Preferred subgroups of compounds of formula I according to the invention are those wherein
$R^1$ is methyl or ethyl;
$R^2$ is chloro, fluoro or methoxy;
$R^3$ is H, chloro or fluoro;
$R^4$ is chloro or fluoro; and
$R^5$ is H or methoxy.

Preferred individual compounds are:
3-chloro-4-(2-chloro-6-fluoro-phenyl)-5-(6-chloro-pyridin-3-yl)-6-methyl-pyridazine;
4-(6-chloro-pyridin-3-yl)-6-methoxy-3-methyl-5-(2,4,6-trifluoro-phenyl)-pyridazine;
3-chloro-5-(6-chloro-pyridin-3-yl)-6-ethyl-4-(2,4,6-trifluoro-phenyl)-pyridazine;
3-chloro-5-(5,6-dichloro-pyridin-3-yl)-6-methyl-4-(2,4,6-trifluoro-phenyl)-pyridazine;
3-chloro-5-(6-chloro-pyridin-3-yl)-4-(2,6-difluoro-4-methoxy-phenyl)-6-methyl-pyridazine;
3-chloro-5-(6-chloro-pyridin-3-yl)-6-isopropyl-4-(2,4,6-trifluoro-phenyl)-pyridazine; and
4-(6-chloro-pyridin-3-yl)-5-(2,6-difluoro-4-methoxyphenyl)-6-methoxy-3-methyl-pyridazine.

Especially preferred individual compounds are:

3-chloro-4-(2-chloro-6-fluoro-phenyl)-5-(6-chloro-pyridin-3-yl)-6-methyl-pyridazine;

4-(6-chloro-pyridin-3-yl)-6-methoxy-3-methyl-5-(2,4,6-trifluoro-phenyl)-pyridazine;

3-chloro-5-(6-chloro-pyridin-3-yl)-6-ethyl-4-(2,4,6-trifluoro-phenyl)-pyridazine; and 3-chloro-5-(5,6-dichloro-pyridin-3-yl)-6-methyl-4-(2,4,6-trifluoro-phenyl)-pyridazine.

Certain pyridazine derivatives with aryl or heteroaryl groups in positions 4 and 5 have been proposed for controlling plant-destructive fungi, for example in WO 2005/121104, WO 2006/001175, WO 2007/066601 and WO 2007/080720. However, the action of those preparations is not satisfactory in all aspects of agricultural needs. Surprisingly, with the compounds of formula I, new kinds of fungicides having a high level of biological activity have now been found.

The compounds of formula I.2, wherein $R^1$, $R^3$, $R^4$ and $R^5$ are as defined for formula I, can be obtained by transformation of a compound of formula I.1, wherein $R^1$, $R^3$, $R^4$ and $R^5$ are as defined for formula I, with methanol and base or with sodium methoide.

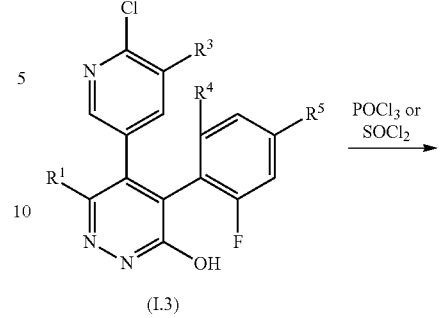

(I.3)

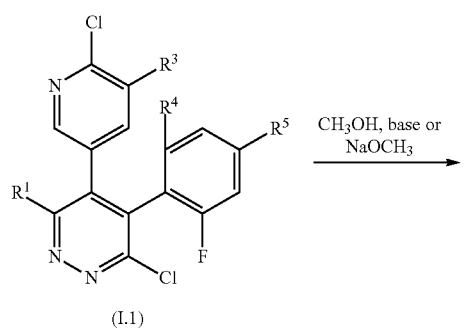

(I.1)

The compounds of formula I.3, wherein $R^1$, $R^3$, $R^4$ and $R^5$ are as defined for formula I, can be obtained by transformation of a compound of formula II, wherein $R^1$, $R^3$, $R^4$ and $R^5$ are as defined for formula I, with a hydrazine derivative, e.g. hydrazine hydrate.

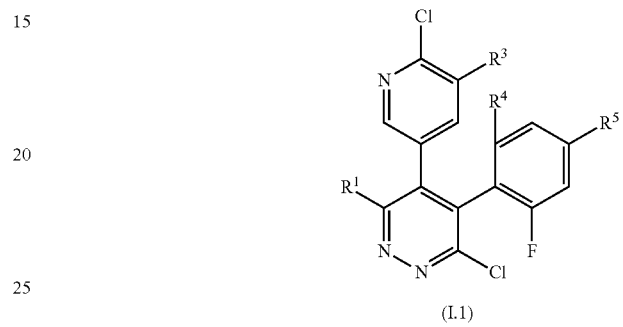

(II)

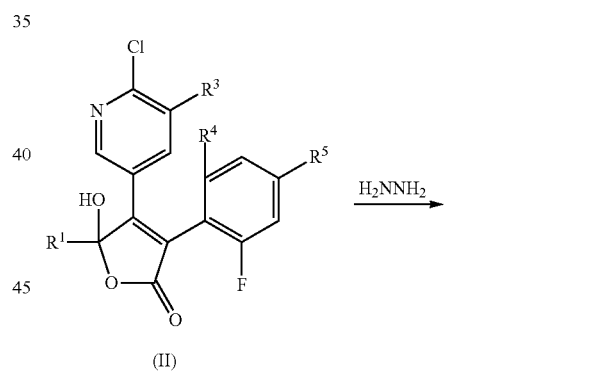

(I.3)

The compounds of formula I.1, wherein $R^1$, $R^3$, $R^4$ and $R^5$ are as defined for formula I, can be obtained by transformation of a compound of formula I.3, wherein $R^1$, $R^3$, $R^4$ and $R^5$ are as defined for formula I, with phosphorus oxychloride or thionyl chloride.

The compounds of formula II, wherein $R^1$, $R^3$, $R^4$ and $R^5$ are as defined for formula I, can be obtained by transformation of a compound of formula III, wherein $R^1$, $R^3$, $R^4$ and $R^5$ are as defined for formula I, by oxidation with oxygen, air or 3-chloroperbenzoic acid.

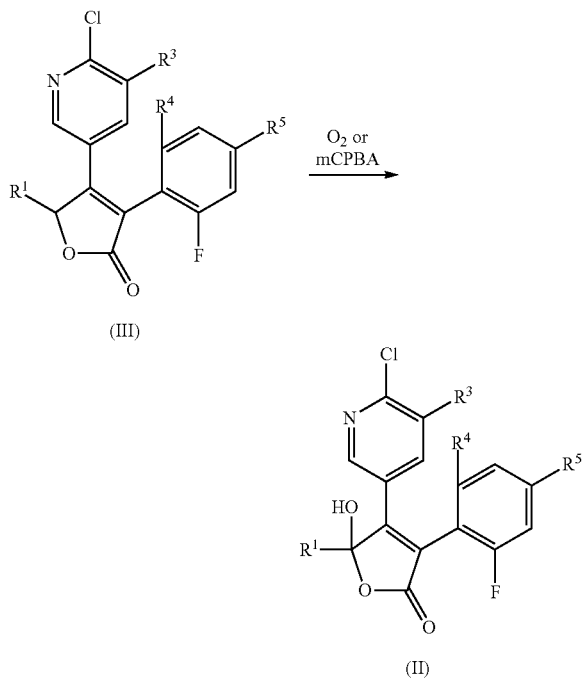

(III)

(II)

The compounds of formula III, wherein $R^1$, $R^3$, $R^4$ and $R^5$ are as defined for formula I, can be obtained by transformation of a compound of formula IV, wherein $R^1$, $R^3$, $R^4$ and $R^5$ are as defined for formula I, with a base, e.g. pyridine, triethylamine, diisopropylethylamine, 1,5-diazabicyclo[4.3.0]non-5-ene or 1,8-diazabicyclo[5.4.0]undec-7-ene.

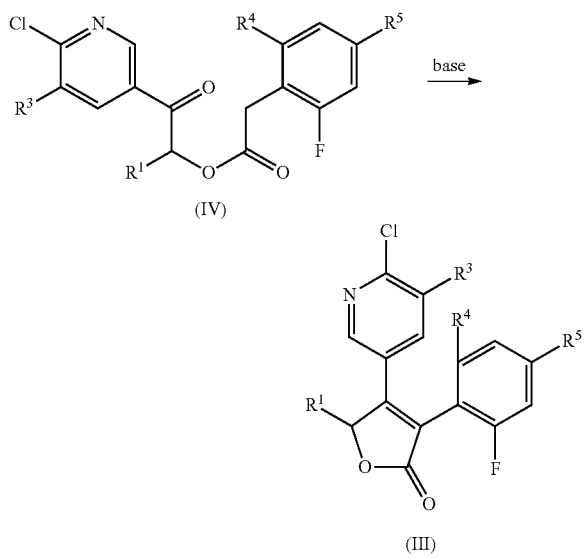

(IV)

(III)

The compounds of formula IV, wherein $R^1$, $R^3$, $R^4$ and $R^5$ are as defined for formula I, can be obtained by transformation of a compound of formula V, wherein $R^1$ and $R^3$ are as defined for formula I and Hal is halogen, preferably chlorine or bromine, with a compound of formula VI, wherein $R^4$ and $R^5$ is as defined for formula I, and a base, e.g. pyridine, triethylamine, diisopropylethylamine, 1,5-diazabicyclo[4.3.0]non-5-ene or 1,8-diazabicyclo[5.4.0]undec-7-ene.

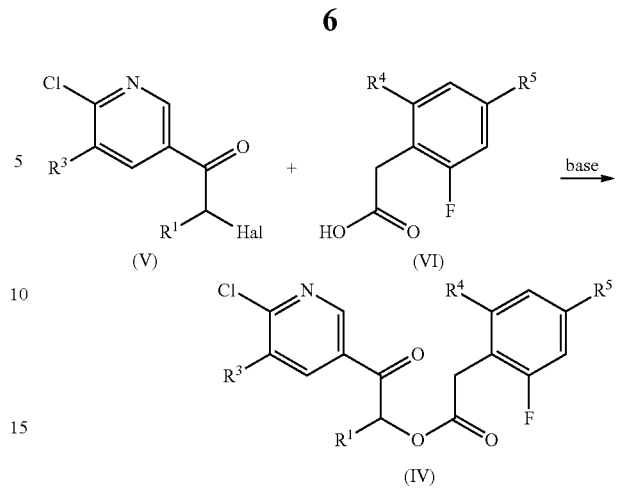

(V)  (VI)

(IV)

Surprisingly, it has now been found that the novel compounds of formula I have, for practical purposes, a very advantageous level of biological activity for protecting plants against diseases that are caused by fungi as well as by bacteria and viruses.

The compounds of formula I can be used in unmodified form or, preferably, together with carriers and adjuvants conventionally employed in the art of formulation.

Therefore the invention also relates to compositions for controlling and protecting against phytopathogenic micro-organisms, comprising a compound of formula I and an inert carrier, and to a method of controlling or preventing infestation of useful plants by phytopathogenic micro-organisms, wherein a composition, comprising a compound of formula I as active ingredient and an inert carrier, is applied to the plants, to parts thereof or the locus thereof.

In addition, the invention could be used to protect non-living materials from fungal attack, e.g. lumber, wall boards and paint.

To this end compounds of formula I and inert carriers are conveniently formulated in known manner to mollifiable concentrates, coat able pastes, directly spray able or dilatable solutions, dilute emulsions, wet table powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or pacifiers as well as fertilizers, micronutrient donors or other formulations for obtaining special effects.

Suitable carriers and adjuvants can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

The compounds of formula I or compositions, comprising a compound of formula I as active ingredient and an inert carrier, can be applied to the locus of the plant or plant to be treated, simultaneously or in succession with further compounds. These further compounds can be e.g. fertilizers or micronutrient donors or other preparations which influence the growth of plants. They can also be selective herbicides, plant growth regulators as well as insecticides, fungicides, bactericides, nematicides, molluscicides or mixtures of several of these preparations, if desired together with further carriers, surfactants or application promoting adjuvants customarily employed in the art of formulation.

A preferred method of applying a compound of formula I, or a composition, comprising a compound of formula I as active ingredient and an inert carrier, is foliar application. The frequency of application and the rate of application will depend on the risk of infestation by the corresponding pathogen. However, the compounds of formula I can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula I may also be applied to seeds (coating) by impregnating the seeds or tubers either with a liquid formulation of the fungicide or coating them with a solid formulation.

A formulation, i.e. a composition comprising the compound of formula I and, if desired, a solid or liquid adjuvant, is prepared in a known manner, typically by intimately mixing and/or grinding the compound with extenders, for example solvents, solid carriers and, optionally, surface-active compounds (surfactants).

The agrochemical formulations will usually contain from 0.1 to 99% by weight, preferably from 0.1 to 95% by weight, of the compound of formula I, 99.9 to 1% by weight, preferably 99.8 to 5% by weight, of a solid or liquid adjuvant, and from 0 to 25% by weight, preferably from 0.1 to 25% by weight, of a surfactant.

Whereas it is preferred to formulate commercial products as concentrates, the end user will normally use dilute formulations.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient rates of application are from 10 mg to 1 g of active substance per kg of seeds. The rate of application for the desired action can be determined by experiments. It depends for example on the type of action, the developmental stage of the useful plant, and on the application (location, timing, application method) and can, owing to these parameters, vary within wide limits.

The invention relates to a method of controlling or preventing infestation of useful plants by phytopathogenic micro-organisms, wherein a compound of formula I is applied as active ingredient to the plants, to parts thereof or the locus thereof. The compounds of formula I according to the invention are distinguished by excellent activity at low rates of application, by being well tolerated by plants and by being environmentally safe. They have very useful curative, preventive and systemic properties and are used for protecting numerous useful plants. The compounds of formula I can be used to inhibit or destroy the diseases that occur on plants or parts of plants (fruit, blossoms, leaves, stems, tubers, roots) of different crops of useful plants, while at the same time protecting also those parts of the plants that grow later e.g. from phytopathogenic micro-organisms.

It is also possible to use compounds of formula I as dressing agents for the treatment of plant propagation material, in particular of seeds (fruit, tubers, grains) and plant cuttings (e.g. rice), for the protection against fungal infections as well as against phytopathogenic fungi occurring in the soil.

Furthermore the compounds of formula I according to the invention may be used for controlling fungi in related areas, for example in the protection of technical materials, including wood and wood related technical products, in food storage or in hygiene management.

Within the scope of the invention, useful plants to be protected typically comprise the following groups of plants: cereals (wheat, barley, rye, oat, rice, maize, sorghum and related species); beets (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucurbit plants (pumpkins, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamomum, camphor) or plants such as tobacco, nuts, coffee, eggplants, sugar cane, tea, pepper, vines, hops, bananas and natural rubber plants, as well as ornamentals.

The term "useful plants" and/or "target crops" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogen-oxidase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" and/or "target crops" is to be understood as including also useful plants which have been so transformed by the use of recombinant DNA techniques that they are capable of synthesising one or more selectively acting toxins, such as are known, for example, from toxin-producing bacteria, especially those of the genus *Bacillus*.

The term "useful plants" and/or "target crops" is to be understood as including also useful plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

The term "locus" of a useful plant as used herein is intended to embrace the place on which the useful plants are growing, where the plant propagation materials of the useful plants are sown or where the plant propagation materials of the useful plants will be placed into the soil. An example for such a locus is a field, on which crop plants are growing.

The term "plant propagation material" is understood to denote generative parts of the plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds.

The compounds of formula I are, for example, effective against the phytopathogenic fungi of the following classes: The compounds of formula I are, for example, effective against the phytopathogenic fungi of the following classes: Fungi imperfecti (e.g. *Alternaria* spp.), *Basidiomycetes* (e.g. *Corticium* spp., *Ceratobasidium* spp., *Waitea* spp., *Thanatephorus* spp., *Rhizoctonia* spp., *Hemileia* spp., *Puccinia* spp., *Phakopsora* spp., *Ustilago* spp., *Tilletia* spp.), *Ascomycetes* (e.g. *Venturia* spp., *Blumeria* spp., *Erysiphe* spp., *Podosphaera* spp., *Uncinula* spp., *Monilinia* spp., *Sclerotinia* spp., *Colletotrichum* spp., *Glomerella* spp., *Fusarium* spp., *Gibberella* spp., *Monographella* spp., *Phaeosphaeria* spp., *Mycosphaerella* spp., *Cercospora* spp., *Pyrenophora* spp., *Rhynchosporium* spp., *Magnaporthe* spp., *Gaeumannomyces* spp., *Oculimacula* spp., *Ramularia* spp., *Botryotinia* spp.) and Oomycetes (e.g. *Phytophthora* spp., *Pythium* spp., *Plasmopara* spp., *Peronospora* spp., *Pseudoperonospora* spp. *Bremia* spp). Outstanding activity has been observed against powdery mildews (e.g. *Uncinula necator*), rusts (e.g. *Puccinia* spp.) and leaf spots (e.g. *Mycosphaerella* spp.). Furthermore, the novel compounds of formula I are effective against phytopathogenic gram negative and gram positive bacteria (e.g. *Xanthomonas* spp, *Pseudomonas* spp, *Erwinia amylovora*, *Ralstonia* spp.) and viruses (e.g. tobacco mosaic virus).

The compounds of formula I are normally used in the form of fungicidal compositions for controlling or protecting against phytopathogenic microorganisms, comprising as active ingredient at least one compound of formula I or at least one preferred individual compound as above-defined, in free form or in agrochemically usable salt form, and at least one of the above-mentioned adjuvants.

Said fungicidal compositions for controlling or protecting against phytopathogenic microorganisms, comprising as active ingredient at least one compound of formula I or at least one preferred individual compound as above-defined, in free form or in agrochemically usable salt form, and at least one of the above-mentioned adjuvants can be mixed with other fungicides, resulting in some cases in unexpected synergistic activities. Mixing components which are particularly preferred are:

Azoles, such as azaconazole, BAY 14120, bitertanol, bromuconazole, cyproconazole, difenoconazole, diniconazole, epoxiconazole, fenbuconazole, fluquinconazole, flusilazole, flutriafol, hexaconazole, imazalil, imibenconazole, ipconazole, metconazole, myclobutanil, pefurazoate, penconazole, prothioconazole, pyrifenox, prochloraz, propiconazole, simeconazole, tebuconazole, tetraconazole, triadimefon, triadimenol, triflumizole, triticonazole;

Pyrimidinyl carbinoles, such as ancymidol, fenarimol, nuarimol;

2-amino-pyrimidines, such as bupirimate, dimethirimol, ethirimol;

Morpholines, such as dodemorph, fenpropidine, fenpropimorph, spiroxamine, tridemorph;

Anilinopyrimidines, such as cyprodinil, mepanipyrim, pyrimethanil;

Pyrroles, such as fenpiclonil, fludioxonil;

Phenylamides, such as benalaxyl, furalaxyl, metalaxyl, R-metalaxyl, ofurace, oxadixyl;

Benzimidazoles, such as benomyl, carbendazim, debacarb, fuberidazole, thiabendazole;

Dicarboximides, such as chlozolinate, dichlozoline, iprodione, myclozoline, procymidone, vinclozoline;

Carboxamides, such as boscalid, carboxin, fenfuram, flutolanil, mepronil, oxycarboxin, penthiopyrad, thifluzamide;

guanidines, such as guazatine, dodine, iminoctadine;

Strobilurines, such as azoxystrobin, dimoxystrobin, enestroburin, fluoxastrobin, kresoxim-methyl, metominostrobin, trifloxystrobin, orysastrobin, picoxystrobin, pyraclostrobin;

Dithiocarbamates, such as ferbam, mancozeb, maneb, metiram, propineb, thiram, zineb, ziram;

N-halomethylthiotetrahydrophthalimides, such as captafol, captan, dichlofluanid, fluoromides, folpet, tolyfluanid;

Cu-compounds, such as Bordeaux mixture, copper hydroxide, copper oxychloride, copper sulfate, cuprous oxide, mancopper, oxine-copper;

Nitrophenol-derivatives, such as dinocap, nitrothal-isopropyl;

Organo-phosphorus-derivatives, such as edifenphos, iprobenphos, isoprothiolane, phosdiphen, pyrazophos, tolclofos-methyl;

Pyridazine-derivatives which are known and may be prepared by methods as described in WO 05/121104, WO 06/001175 and WO 07/066601, such as 3-chloro-5-(4-chloro-phenyl)-6-methyl-4-(2,4,6-trifluoro-phenyl)-pyridazine (formula P.1), 3-chloro-6-methyl-5-p-tolyl-4-(2,4,6-trifluoro-phenyl)-pyridazine (formula P.2) and 3-chloro-4-(3-chloro-5-methoxy-pyridin-2-yl)-5-(4-chloro-phenyl)-6-methyl-pyridazine (formula P.3);

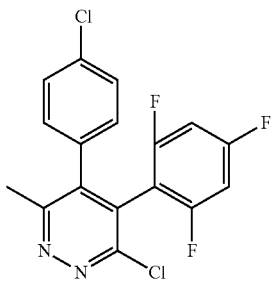

P.1

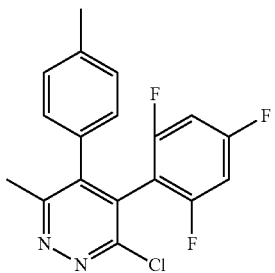

P.2

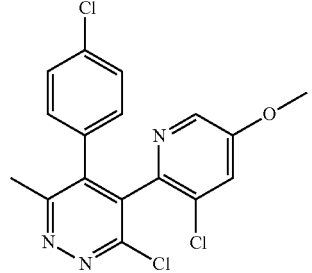

P.3

Triazolopyrimidine derivatives which are known and may be prepared by methods as described in WO98/46607, such as 5-chloro-7-(4-methyl-piperidin-1-yl)-6-(2,4,6-trifluoro-phenyl)-[1,2,4]triazolo[1,5-a]pyrimidine (formula T.1);

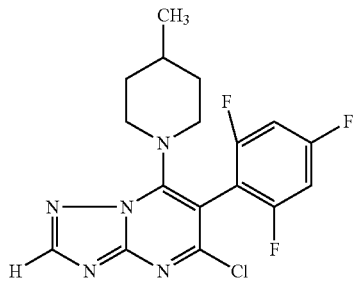

Carboxamide derivatives which are known and may be prepared by methods as described in WO04/035589, WO06/37632, WO03/074491 or WO03070705, such as 3-difluoromethyl-1-methyl-1H-pyrazole-4-carboxylic acid (9-isopropyp-1,2,3,4-tetrahaydro-1,4-methano-naphthalen-5-yl)-amide (formula U.1), 3-difluoromethyl-1-methyl-1H-pyrazole-4-carboxylic acid (2-bicyclopropyl-2-yl-phenyl)-amide (formula U.2) or N-(3',4'-dichloro-5-fluoro-1,1'-biphenyl-2-yl)-3-(difluoromethyl)-1-methyl-1H-pyrazole-4-carboxamide;

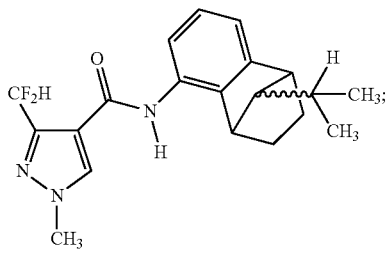

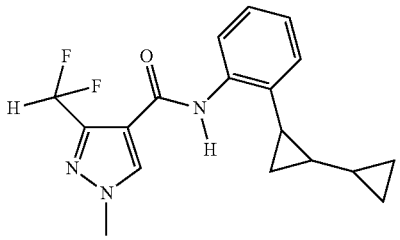

Benzamide derivatives which are known and may be prepared by methods as described in WO 2004/016088, such as N-{-2-[3-chloro-5-(trifluoromethyl)-2-pyridinyl]ethyl}-2-trifluoromethylbenzamide, which is also known under the name fluopyram (formula V.1);

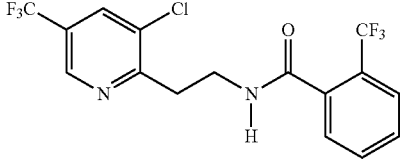

and

Various others, such as acibenzolar-S-methyl, anilazine, benthiavalicarb, blasticidin-S, chinomethionate, chloroneb, chlorothalonil, cyflufenamid, cymoxanil, dichlone, diclocymet, diclomezine, dicloran, diethofencarb, dimethomorph, flumorph, dithianon, ethaboxam, etridiazole, famoxadone, fenamidone, fenoxanil, fentin, ferimzone, fluazinam, fluopicolide, flusulfamide, fenhexamid, fosetyl-aluminium, hymexazol, iprovalicarb, cyazofamid, kasugamycin, mandipropamid, methasulfocarb, metrafenone, nicobifen, pencycuron, phthalide, polyoxins, probenazole, propamocarb, proquinazid, pyroquilon, quinoxyfen, quintozene, sulfur, tiadinil, triazoxide, tricyclazole, triforine, validamycin, zoxamide and glyphosate.

Another aspect of invention is related to the use of a compound of formula I or of a preferred individual compound as above-defined, of a composition comprising at least one compound of formula I or at least one preferred individual compound as above-defined, or of a fungicidal mixture comprising at least one compound of formula I or at least one preferred individual compound as above-defined, in admixture with other fungicides, as described above, for controlling or preventing infestation of plants, harvested food crops, seeds or non-living materials by phytopathogenic microorganisms, preferably fungal organisms.

A further aspect of invention is related to a method of controlling or preventing an infestation of crop plants, harvested food crops or of non-living materials by phytopathogenic or spoilage microorganisms or organisms potentially harmful to man, especially fungal organisms, which comprises the application of a compound of formula I or of a preferred individual compound as above-defined as active ingredient to the plants, to parts of the plants or to the locus thereof, to seeds or to any part of the non-living materials.

Controlling or preventing means reducing the infestation of crop plants or of non-living materials by phytopathogenic or spoilage microorganisms or organisms potentially harmful to man, especially fungal organisms, to such a level that an improvement is demonstrated.

Surprisingly, the pyridazine compounds of formula I according to the invention, in particular the individual pyridazine compounds described in the above description as being preferred, also present a plant growth regulator (PGR) activity. Therefore, the present invention also relates to the use of these novel pyridazine derivatives as plant growth regulators (PGRs).

Plant growth regulators (PGRs) are generally any substances or mixtures of substances intended to accelerate or retard the rate of growth or maturation, or otherwise alter the development of plants or their produce.

Plant growth regulators (PGRs) affect growth and differentiation of plants.

More specifically, various plant growth regulators (PGRs) can, for example, reduce plant height, stimulate seed germination, induce flowering, darken leaf coloring, change the rate of plant growth and modify the timing and efficiency of fruiting.

Furthermore, the present invention also relates to compositions comprising the novel pyridazine derivatives of the present invention that improve plants, a process which is commonly and hereinafter referred to as "plant health".

For example, advantageous properties that may be mentioned are improved crop characteristics including: emergence, crop yields, protein content, increased vigour, faster maturation, increased speed of seed emergence, improved nitrogen utilization efficiency, improved water use efficiency, improved oil content and/or quality, improved digestibility, faster ripening, improved flavor, improved starch content, more developed root system (improved root growth), improved stress tolerance (e.g. against drought, heat, salt, light, UV, water, cold), reduced ethylene (reduced production and/or inhibition of reception), tillering increase, increase in plant height, bigger leaf blade, less dead basal leaves, stronger tillers, greener leaf color, pigment content, photosynthetic activity, less input needed (such as fertilizers or water), less seeds needed, more productive tillers, earlier flowering, early grain maturity, less plant verse (lodging), increased shoot growth, enhanced plant vigor, increased plant stand and early and better germination.

Advantageous properties, obtained especially from treaded seeds, are e.g. improved germination and field establishment, better vigor, more homogeneous field establishment.

Advantageous properties, obtained especially from foliar and/or in-furrow application are e.g. improved plant growth and plant development, better growth, more tillers, greener leafes, largers leaves, more biomass, better roots, improved stress tolerance of the plants, more grain yield, more biomass harvested, improved quality of the harvest (content of fatty acids, metabolites, oil etc), more marketable products (e.g. improved size), improved process (e.g. longer shelf-life, better extraction of compounds), improved quality of seeds (for being seeded in the following seasons for seed production); or any other advantages familiar to a person skilled in the art.

It is therefore an object of the present invention to provide a method which solves the problems outlined above.

The present invention relates to plant-protecting active ingredients that are pyridazine compounds of formula I according to the invention, in particular the individual pyridazine compounds described in the above description as being preferred, and mixtures with increased efficacy and to a method of improving the health of plants by applying said compounds and mixtures to the plants or the locus thereof.

The action of the compounds of formula I goes beyond the known fungicidal action. The pyridazine compounds of formula I according to the invention, in particular the individual pyridazine compounds described in the above description as being preferred compounds exhibit plant health The term plant health comprises various sorts of improvements of plants that are not connected to the control of harmful fungi.

In another aspect, the present invention relates to a composition comprising at least one compound of formula I or at least one preferred individual compound as above-defined and/or at least one pharmaceutically acceptable salt thereof; at least one pharmaceutically acceptable carrier and/or at least one pharmaceutically acceptable diluent.

In a further aspect, the present invention also relates to a compound of formula I or a preferred individual compound as above-defined, or a pharmaceutically acceptable salt thereof for use as a medicament.

In a preferred aspect, the present invention also relates to a compound of formula I or of a preferred individual compound as above-defined, or a pharmaceutically acceptable salt thereof for the treatment of cancer.

In an additional aspect, the present invention also relates to the use of a compound formula I or of a preferred individual compound as above-defined, or a pharmaceutically acceptable salt thereof in the manufacture of a medicament for the treatment of cancer.

In a particular aspect, the present invention also relates to a method of treating cancer in a subject in need thereof, comprising administering a compound formula I or a preferred individual compound as above-defined to said subject in an amount effective to treat said cancer.

The invention further provides fungicidal or pharmaceutical compositions comprising a compound of formula I or a preferred individual compound as above-defined, and/or their agriculturally or pharmaceutically acceptable salts and suitable carriers.

Suitable pharmaceutically acceptable carriers are described below.

The pyridazine compounds of formula I according to the invention, in particular the individual pyridazine compounds described in the above description as being preferred, and/or their pharmaceutically acceptable salts are suitable for the treatment, inhibiton or control of growth and/or propagation of tumor cells and the disorders associated therewith.

Accordingly, they are suitable for cancer therapy in warm-blooded vertebrates, for example mammals and birds, in particular man, but also other mammals, in particular useful and domestic animals, such as dogs, cats, pigs, ruminants (cattle, sheep, goats, bison, etc.), horses and birds, such as chicken, turkey, ducks, geese, guineafowl and the like.

The pyridazine compounds of formula I according to the invention, in particular the individual pyridazine compounds described in the above description as being preferred, and/or their pharmaceutically acceptable salts are suitable for the therapy of cancer or cancerous disorders of the following organs: breast, lung, intestine, prostate, skin (melanoma), kidney, bladder, mouth, larynx, oesophagus, stomach, ovaries, pancreas, liver and brain.

In addition to pyridazine compounds of formula I according to the invention, in particular the individual pyridazine compounds described in the above description as being preferred, and/or its pharmaceutically acceptable salt, the pharmaceutical compositions according to the invention comprise at least optionally a suitable carrier.

"Pharmaceutically acceptable" means compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Suitable carriers are, for example, solvents, carriers, excipients, binders and the like customarily used for pharmaceutical formulations, which are described below in an exemplary manner for individual types of administration.

"Pharmaceutically acceptable carrier" as used herein means a pharmaceutically-acceptable material, composition or vehicle, such as a liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include:

sugars, such as lactose, glucose and sucrose;
starches, such as corn starch and potato starch;
cellulose, and its derivatives, such as sodium carboxymethyl cellulose, ethyl cellulose and cellulose acetate;
powdered tragacanth;
malt;
gelatin;
talc;
excipients, such as cocoa butter and suppository waxes;
oils, such as peanut oil, cottonseed oil, safflower oil, sesame oil, olive oil, corn oil and soybean oil;
glycols, such as propylene glycol;

polyols, such as glycerin, sorbitol, mannitol and polyethylene glycol;

esters, such as ethyl oleate and ethyl laurate;

agar; buffering agents, such as magnesium hydroxide and aluminum hydroxide;

alginic acid;

pyrogen-free water;

isotonic saline;

Ringer's solution;

ethyl alcohol;

phosphate buffer solutions; and other non-toxic compatible substances employed in pharmaceutical formulations.

The pyridazine compounds of formula I according to the invention, in particular the individual pyridazine compounds described in the above description as being preferred (the active compound), can be administered in a customary manner, for example orally, intravenously, intramuscularly or subcutaneously.

For oral administration, the active compound can be mixed, for example, with an inert diluent or with an edible carrier; it can be embedded into a hard or soft gelatin capsule, it can be compressed to tablets or it can be mixed directly with the food/feed.

The active compound can be mixed with excipients and administered in the form of indigestible tablets, buccal tablets, pastilles, pills, capsules, suspensions, potions, syrups and the like.

Such preparations should contain at least 0.1% of active compound.

The composition of the preparation may, of course, vary.

It usually comprises from 2 to 60% by weight of active compound, based on the total weight of the preparation in question (dosage unit).

Preferred preparations of the pyridazine compounds of formula I according to the invention, in particular the individual pyridazine compounds described in the above description as being preferred, comprise from 10 to 1000 mg of active compound per oral dosage unit.

The tablets, pastilles, pills, capsules and the like may furthermore comprise the following components: binders, such as traganth, gum arabic, corn starch or gelatin, excipients, such as dicalcium phosphate, disintegrants, such as corn starch, potato starch, alginic acid and the like, glidants, such as magnesium stearate, sweeteners, such as sucrose, lactose or saccharin, and/or flavors, such as peppermint, vanilla and the like.

Capsules may furthermore comprise a liquid carrier.

Other substances which modify the properties of the dosage unit may also be used.

For example, tablets, pills and capsules may be coated with schellack, sugar or mixtures thereof.

In addition to the active compound, syrups or potions may also comprise sugar (or other sweeteners), methyl- or propylparaben as preservative, a colorant and/or a flavor.

The components of the active compound preparations must, of course, be pharmaceutically pure and nontoxic at the quantities employed.

Furthermore, the active compounds can be formulated as preparations with a controlled release of active compound, for example as delayed-release preparations.

The active compounds can also be administered parenterally or intraperitoneally.

Solutions or suspensions of the active compounds or their salts can be prepared with water using suitable wetting agents, such as hydroxypropylcellulose.

Dispersions can also be prepared using glycerol, liquid polyethylene glycols and mixtures thereof in oils.

Frequently, these preparations furthermore comprise a preservative to prevent the growth of microorganisms.

Preparations intended for injections comprise sterile aqueous solutions and dispersions and also sterile powders for preparing sterile solutions and dispersions.

The preparation has to be sufficiently liquid for injection.

It has to be stable under the preparation and storage conditions and it has to be protected against contamination by microorganisms.

The carrier may be a solvent or a dispersion medium, for example, water, ethanol, a polyol (for example glycerol, propylene glycol or liquid polyethylene glycol), a mixture thereof and/or a vegetable oil.

Pharmaceutical compositions of this invention suitable for parenteral administration comprise an pyridazine compound of formula I according to the invention, in particular an individual pyridazine compounds described in the above description as being preferred, in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. These compositions may also contain adjuvants such as preservatives, wetting agents, emulsifying agents and dispersing agents. Prevention of the action of microorganisms may be ensured by the inclusion of various antibacterial and other antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

The pharmaceutical compositions of the present invention may be given by any suitable means of administration including orally, parenterally, topically, transdermally or rectally. They are of course given by forms suitable for each administration route. For example, they are administered in tablets or capsule form, by injection, inhalation, eye lotion, ointment, suppository, administration by injection, infusion or inhalation; topical by lotion or ointment; and rectal by suppositories. Topical or parenteral administration is preferred.

The following non-limiting examples illustrate the above-described invention in more detail.

EXAMPLE 1

This Example Illustrates the Preparation of 3-chloro-4-(2-chloro-6-fluoro-phenyl)-5-(6-chloro-pyridin-3-yl)-6-methyl-pyridazine (Compound No. I.a.02)

a) Preparation of 2-bromo-1-(6-chloro-pyridin-3-yl)-propan-1-one

Bromine (45.4 g) is slowly added to the mixture of 1-(6-chloro-pyridin-3-yl)-propan-1-one (48.2 g), 0.4 ml of hydrobromic acid (33% solution in acetic acid) and 250 ml of acetic acid at room temperature under a nitrogen atmosphere. Subsequently, the mixture is slowly heated to 80° C. The reaction mixture is stirred at 80° C. for 30 min, during which a yellow suspension is formed, then cooled down to 10° C. and filtered. The solid remainder is washed with tert-butyl methyl ether to deliver 2-bromo-1-(6-chloro-pyridin-3-yl)-propan-1-one hydrobromide as a yellowish solid. To a suspension of this intermediate in 800 ml of tert-butyl methyl ether is added 400 ml of a saturated aqueous sodium bicarbonate solution and the reaction mixture is stirred for 15 min. The phases are separated, the organic layer is washed with brine, dried over sodium sulfate and concentrated under reduced pressure to obtain 2-bromo-1-(6-chloro-pyridin-3-yl)-propan-1-one as an oil.

b) Preparation of 3-(2-chloro-6-fluoro-phenyl)-4-(6-chloro-pyridin-3-yl)-5-hydroxy-5-methyl-5H-furan-2-one (Compound No. II.a.1)

Triethylamine (1.0 g) is slowly added to a solution of 2-bromo-1-(6-chloro-pyridin-3-yl)-propan-1-one (2.5 g), 2-chloro-6-fluorophenylacetic acid (1.9 g) in 50 ml of acetonitrile and this mixture is stirred for 16 h at room temperature. Subsequently 1,8-diazabicyclo[5.4.0]undec-7-ene (DBU, 3.4 g) is slowly added under cooling and stirring is continued for further 2 h. Then air is blown through the reaction mixture for 3 h. The reaction mixture is poured into an aqueous ammonium chloride solution and the mixture is extracted with ethyl acetate. The combined organic layer is washed with brine, dried over sodium sulfate and evaporated under reduced pressure. The remainder is purified by chromatography on silica gel, using a mixture of heptane/ethyl acetate 2:1 as eluent to obtain 3-(2-chloro-6-fluoro-phenyl)-4-(6-chloro-pyridin-3-yl)-5-hydroxy-5-methyl-5H-furan-2-one (Compound No. II.a.1) as white foam.

c) Preparation of 4-(2-chloro-6-fluoro-phenyl)-5-(6-chloro-pyridin-3-yl)-6-methyl-2H-pyridazin-3-one (Compound No. I.a.01)

Hydrazine hydrate (12 g) is added to a solution of 3-(2-chloro-6-fluoro-phenyl)-4-(6-chloro-pyridin-3-yl)-5-hydroxy-5-methyl-5H-furan-2-one (Compound No. II.a.1, 80 g) in 400 ml of 1-butanol and this mixture is heated for 7 h to 120° C. Subsequently, the mixture is poured into 400 ml of tert-butyl methyl ether. The resulting mixture is stirred for 30 min, then cooled to 0° C. and filtered. The solid remainder is washed with tert-butyl methyl ether to deliver 4-(2-chloro-6-fluoro-phenyl)-5-(6-chloro-pyridin-3-yl)-6-methyl-2H-pyridazin-3-one (Compound No. I.a.01) as colourless solid.

d) A mixture of 4-(2-chloro-6-fluoro-phenyl)-5-(6-chloro-pyridin-3-yl)-6-methyl-2H-pyridazin-3-one (Compound No. I.a.01, 57 g)

and 160 ml of phosphorus oxychloride is heated at 110° C. for 1 h. After cooling the reaction mixture is evaporated under reduced pressure. The remainder is taken up with ethyl acetate and water and the phases are separated. The organic layer is washed with water and brine, dried over sodium sulfate and evaporated under reduced pressure. The residue is recrystallised from toluene to deliver 3-chloro-4-(2-chloro-6-fluoro-phenyl)-5-(6-chloro-pyridin-3-yl)-6-methyl-pyridazine (Compound No. I.a.02) as beige crystals, m.p. 166-167° C.

EXAMPLE 2

This Example Illustrates the Preparation of 4-(6-chloro-pyridin-3-yl)-6-methoxy-3-methyl-5-(2,4,6-trifluoro-phenyl)-pyridazine (Compound No. I.a.12)

A mixture of 3-chloro-5-(6-chloro-pyridin-3-yl)-6-methyl-4-(2,4,6-trifluorophenyl)-pyridazine (Compound No. I.a.11, 700 mg), sodium methoxide (30% solution in methanol, 750 mg) and 10 ml of methanol is heated for 6 h to 60° C. Subsequently the reaction mixture is cooled, diluted with water and extracted with ethyl acetate. The combined organic layer is washed with water and brine, dried over sodium sulfate and evaporated under reduced pressure. The remainder is purified by chromatography on silica gel, using a mixture of heptane/ethyl acetate 3:1 as eluent to obtain 4-(6-chloro-pyridin-3-yl)-6-methoxy-3-methyl-5-(2,4,6-trifluoro-phenyl)-pyridazine (Compound I.a.12), m.p. 123-124° C.

Tables 1 and 2 below illustrate examples of individual compounds of formula I and formula II according to the invention.

TABLE 1 individual compounds of formula I according to the invention

| Compound No. | $R^1$ | $R^6$ | $R^2$ |
|---|---|---|---|
| 01 | $CH_3$ | 2-chloro-6-fluoro-phenyl | OH |
| 02 | $CH_3$ | 2-chloro-6-fluoro-phenyl | Cl |
| 03 | $CH_3$ | 2-chloro-6-fluoro-phenyl | $OCH_3$ |
| 04 | $CH_2CH_3$ | 2-chloro-6-fluoro-phenyl | OH |
| 05 | $CH_2CH_3$ | 2-chloro-6-fluoro-phenyl | Cl |
| 06 | $CH_2CH_3$ | 2-chloro-6-fluoro-phenyl | $OCH_3$ |
| 07 | $CH(CH_3)_2$ | 2-chloro-6-fluoro-phenyl | OH |
| 08 | $CH(CH_3)_2$ | 2-chloro-6-fluoro-phenyl | Cl |
| 09 | $CH(CH_3)_2$ | 2-chloro-6-fluoro-phenyl | $OCH_3$ |
| 10 | $CH_3$ | 2,4,6-trifluoro-phenyl | OH |
| 11 | $CH_3$ | 2,4,6-trifluoro-phenyl | Cl |
| 12 | $CH_3$ | 2,4,6-trifluoro-phenyl | $OCH_3$ |
| 13 | $CH_2CH_3$ | 2,4,6-trifluoro-phenyl | OH |
| 14 | $CH_2CH_3$ | 2,4,6-trifluoro-phenyl | Cl |
| 15 | $CH_2CH_3$ | 2,4,6-trifluoro-phenyl | $OCH_3$ |
| 16 | $CH(CH_3)_2$ | 2,4,6-trifluoro-phenyl | OH |
| 17 | $CH(CH_3)_2$ | 2,4,6-trifluoro-phenyl | Cl |
| 18 | $CH(CH_3)_2$ | 2,4,6-trifluoro-phenyl | $OCH_3$ |
| 19 | $CH_3$ | 2,6-difluoro-4-methoxy-phenyl | OH |
| 20 | $CH_3$ | 2,6-difluoro-4-methoxy-phenyl | Cl |
| 21 | $CH_3$ | 2,6-difluoro-4-methoxy-phenyl | $OCH_3$ |
| 22 | $CH_2CH_3$ | 2,6-difluoro-4-methoxy-phenyl | OH |
| 23 | $CH_2CH_3$ | 2,6-difluoro-4-methoxy-phenyl | Cl |
| 24 | $CH_2CH_3$ | 2,6-difluoro-4-methoxy-phenyl | $OCH_3$ |
| 25 | $CH(CH_3)_2$ | 2,6-difluoro-4-methoxy-phenyl | OH |
| 26 | $CH(CH_3)_2$ | 2,6-difluoro-4-methoxy-phenyl | Cl |
| 27 | $CH(CH_3)_2$ | 2,6-difluoro-4-methoxy-phenyl | $OCH_3$ |

As shown above, Table 1 provides 27 specific compounds of Formula (I). Structural examples of these compounds are shown below in Formulas (I.a) through (I.g) wherein $R^1$, $R^2$ and $R^6$ are defined in Table 1.

a) Formula (I.a):

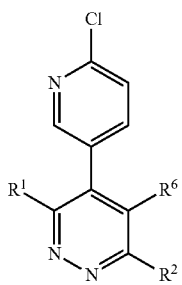
(I.a)

b) Formula (I.b):

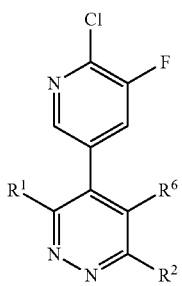
(I.b)

c) Formula (I.c):

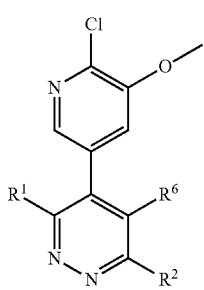
(I.c)

d) Formula (I.d):

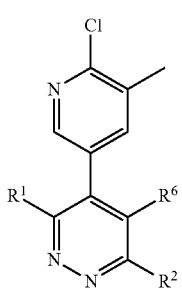
(I.d)

e) Formula (I.e):

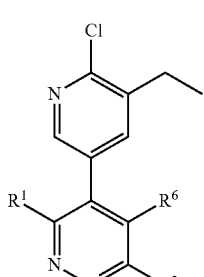
(I.e)

f) Formula (I.f):

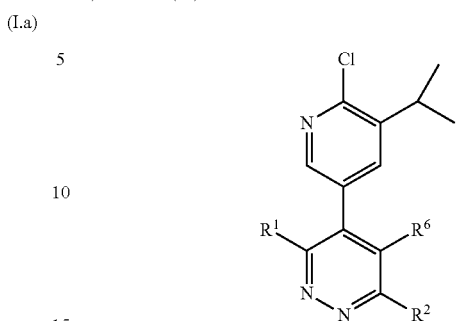
(I.f)

g) Formula (I.g):

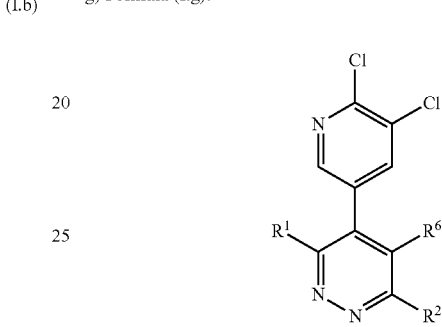
(I.g)

TABLE 2 individual compounds of formula II according to the invention

| Compound No. | $R^1$ | $R^6$ |
|---|---|---|
| 1 | $CH_3$ | 2-chloro-6-fluoro-phenyl |
| 2 | $CH_2CH_3$ | 2-chloro-6-fluoro-phenyl |
| 3 | $CH(CH_3)_2$ | 2-chloro-6-fluoro-phenyl |
| 4 | $CH_3$ | 2,4,6-trifluoro-phenyl |
| 5 | $CH_2CH_3$ | 2,4,6-trifluoro-phenyl |
| 6 | $CH(CH_3)_2$ | 2,4,6-trifluoro-phenyl |
| 7 | $CH_3$ | 2,6-difluoro-4-methoxy-phenyl |
| 8 | $CH_2CH_3$ | 2,6-difluoro-4-methoxy-phenyl |
| 9 | $CH(CH_3)_2$ | 2,6-difluoro-4-methoxy-phenyl |

As shown above, Table 2 provides 9 specific compounds of Formula (II). Structural examples of these compounds are shown below in Formulas (II.a) through (II.g) wherein $R^1$ and $R^6$ are defined in Table 2.

a) Formula (II.a):

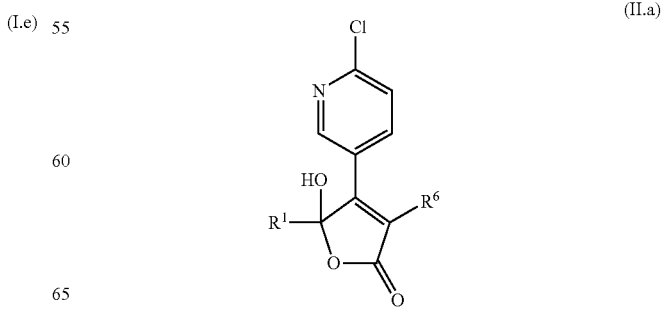
(II.a)

b) Formula (II.b):

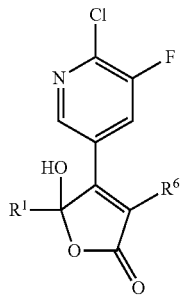

c) Formula (II.c):

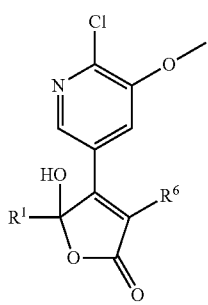

d) Formula (II.d):

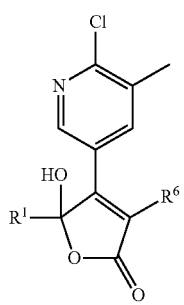

e) Formula (II.e):

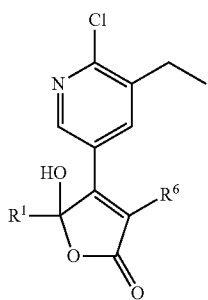

f) Formula (II.f):

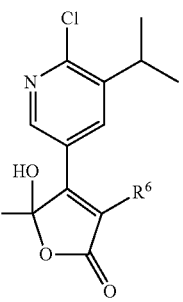

g) Formula (II.g):

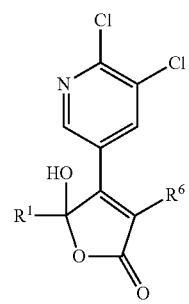

Table 3 shows selected melting point for compounds of Tables 1 and 2. Temperatures are given in degrees Celsius.

TABLE 3

| Melting point for compounds of Tables 1 and 2 | |
| --- | --- |
| Compound Number | m.p. (° C.) |
| I.a.02 | 166-167 |
| I.a.12 | 123-124 |
| I.a.14 | 125-126 |
| I.a.20 | 148-149 |
| I.a.17 | 146-149 |
| I.g.11 | 185-188 |

The compounds according to the present invention can be prepared according to the above-mentioned reaction schemes, in which, unless otherwise stated, the definition of each variable is as defined above for a compound of formula (I).

BIOLOGICAL EXAMPLES

*Alternaria solani*/Tomato/Preventive (Action Against *Alternaria* on Tomato)

4 weeks old tomato plants cv. Roter Gnom are treated with the formulated test compound in a spray chamber. Two days after application tomato plants are inoculated by spraying a spore suspension on the test plants. After an incubation period of 4 days at 22° C./18° C. and 95% r. h. in a greenhouse the disease incidence is assessed.

Compounds I.a.02, I.a.12, I.a.14 and I.a.20 according to the invention at 200 ppm inhibit fungal infestation in this test to at least 80%, while under the same conditions untreated control plants are infected by the phytopathogenic fungi to over 80%.

*Botryotinia fuckeliana* (*Botrytis cinerea*)/Tomato/Preventive (Action Against *Botrytis* on Tomato)

4 weeks old tomato plants cv. Roter Gnom are treated with the formulated test compound in a spray chamber. Two days after application tomato plants are inoculated by spraying a spore suspension on the test plants. After an incubation period of 3 days at 20° C. and 95% r. h. in a greenhouse the disease incidence is assessed.

Compounds I.a.02 and I.a.12 according to the invention at 200 ppm inhibit fungal infestation in this test to at least 80%, while under the same conditions untreated control plants are infected by the phytopathogenic fungi to over 80%.

*Puccinia recondite* f. sp. *tritici*/Wheat/Preventive (Action Against Brown Rust on Wheat)

1 week old wheat plants cv. Arina are treated with the formulated test compound in a spray chamber. One day after application wheat plants are inoculated by spraying a spore suspension (1×105 uredospores/ml) on the test plants. After an incubation period of 1 day at 20° C. and 95% r. h. plants are kept for 10 days 20° C./18° C. (day/night) and 60% r. h. in a greenhouse. The disease incidence is assessed 11 days after inoculation.

Compounds I.a.02, I.a.12, I.a.14 and I.a.20 according to the invention at 200 ppm inhibit fungal infestation in this test to at least 80%, while under the same conditions untreated control plants are infected by the phytopathogenic fungi to over 80%.

*Magnaporthe qrisea* (*Pyricularia oryzae*)/Rice/Preventive (Action Against Rice Blast)

3 weeks old rice plants cv. Koshihikari are treated with the formulated test compound in a spray chamber. Two days after application rice plants are inoculated by spraying a spore suspension (1×10$^5$ conidia/ml) on the test plants. After an incubation period of 6 days at 25° C. and 95% r. h. the disease incidence is assessed.

Compounds I.a.02, I.a.14, I.a.20 and I.g.11 according to the invention at 200 ppm inhibit fungal infestation in this test to at least 80%, while under the same conditions untreated control plants are infected by the phytopathogenic fungi to over 80%.

*Pyrenophora teres* (*Helminthosporium teres*)/Barley/Preventive (Action Against Net Blotch on Barley)

1-week-old barley plants cv. Regina are treated with the formulated test compound in a spray chamber. Two days after application barley plants are inoculated by spraying a spore suspension (2.6×10$^4$ conidia/ml) on the test plants. After an incubation period of 4 days at 20° C. and 95% r. h. the disease incidence is assessed.

Compounds I.a.02, I.a.12, I.a.14 and I.a.20 according to the invention at 200 ppm inhibit fungal infestation in this test to at least 80%, while under the same conditions untreated control plants are infected by the phytopathogenic fungi to over 80%.

*Mycosphaerella graminicola* (*Septoria tritici*)/Wheat/Preventive (Action Against *Septoria* Leaf Spot on Wheat)

2 weeks old wheat plants cv. Riband are treated with the formulated test compound in a spray chamber. One day after application wheat plants are inoculated by spraying a spore suspension (10$^6$ conidia/ml) on the test plants. After an incubation period of 1 day at 22° C./21° C. and 95% r. h. plants are kept at 22° C./21° C. and 70% r.h. in a greenhouse. The disease incidence is assessed 16-18 days after inoculation.

Compounds I.a.02, I.a.14 and I.a.20 according to the invention at 200 ppm inhibits fungal infestation in this test to at least 80%, while under the same conditions untreated control plants are infected by the phytopathogenic fungi to over 80%.

*Uncinula necator* (*Erysiphe necator*)/Grape/Preventive (Action Against Powdery Mildew on Grape)

5 weeks old grape seedlings cv. Gutedel are treated with the formulated test compound in a spray chamber. One day after application grape plants are inoculated by shaking plants infected with grape powdery mildew above the test plants. After an incubation period of 7 days at 24° C./22° C. and 70% r. h. under a light regime of 14/10 h (light/dark) the disease incidence is assessed.

Compounds I.a.02, I.a.12, I.a.14 and I.g.11 according to the invention at 200 ppm inhibit fungal infestation in this test to at least 80%, while under the same conditions untreated control plants are infected by the phytopathogenic fungi to over 80%.

What is claimed is:
1. A compound of formula I:

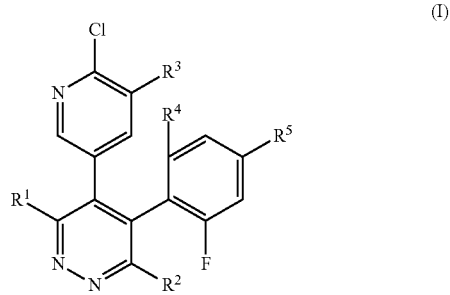

wherein
$R^1$ is methyl, ethyl or isopropyl;
$R^2$ is chloro, fluoro, hydroxy or $C_1$-$C_2$alkoxy;
$R^3$ is H, chloro, fluoro, methoxy or $C_1$-$C_3$alkyl;
$R^4$ is chloro, fluoro or bromo; and
$R^5$ is H, fluoro or methoxy;
or an agrochemically usable salt form thereof;
with the proviso that when $R^1$ is methyl, $R^2$ is chloro and $R^3$ is H, then $R^4$ or $R^5$ is different from fluoro.

2. The compound according to claim 1 wherein
$R^1$ is methyl or ethyl;
$R^2$ is chloro, fluoro or methoxy;
$R^3$ is H, chloro or fluoro;
$R^4$ is chloro or fluoro; and
$R^5$ is H or methoxy.

3. The compound according to claim 1 selected from
3-chloro-4-(2-chloro-6-fluoro-phenyl)-5-(6-chloro-pyridin-3-yl)-6-methyl-pyridazine;
4-(6-chloro-pyridin-3-yl)-6-methoxy-3-methyl-5-(2,4,6-trifluoro-phenyl)-pyridazine;
3-chloro-5-(6-chloro-pyridin-3-yl)-6-ethyl-4-(2,4,6-trifluoro-phenyl)-pyridazine;
3-chloro-5-(5,6-dichloro-pyridin-3-yl)-6-methyl-4-(2,4,6-trifluoro-phenyl)-pyridazine;
3-chloro-5-(6-chloro-pyridin-3-yl)-4-(2,6-difluoro-4-methoxy-phenyl)-6-methyl-pyridazine;
3-chloro-5-(6-chloro-pyridin-3-yl)-6-isopropyl-4-(2,4,6-trifluoro-phenyl)-pyridazine; and
4-(6-chloro-pyridin-3-yl)-5-(2,6-difluoro-4-methoxyphenyl)-6-methoxy-3-methyl-pyridazine.

4. The compound according to claim 3 selected from
3-chloro-4-(2-chloro-6-fluoro-phenyl)-5-(6-chloro-pyridin-3-yl)-6-methyl-pyridazine;
4-(6-chloro-pyridin-3-yl)-6-methoxy-3-methyl-5-(2,4,6-trifluoro-phenyl)-pyridazine;
3-chloro-5-(6-chloro-pyridin-3-yl)-6-ethyl-4-(2,4,6-trifluoro-phenyl)-pyridazine; and
3-chloro-5-(5,6-dichloro-pyridin-3-yl)-6-methyl-4-(2,4,6-trifluoro-phenyl)-pyridazine.

5. A process for the preparation of a compound of formula I.2, (I.2)

wherein $R^1$, $R^3$, $R^4$ and $R^5$ are as defined for compound of formula I, which comprises reacting a compound of formula I.1, (I.1)

wherein $R^1$, $R^3$, $R^4$ and $R^5$ are as defined for compound of formula I, with methanol and base or with sodium methoxide.

6. A process for the preparation of a compound of formula I.1, (I.1)

wherein $R^1$, $R^3$, $R^4$ and $R^5$ are as defined for compound of formula I, which comprises reacting a compound of formula I.3, (I.3)

wherein $R^1$, $R^3$, $R^4$ and $R^5$ are as defined for compound of formula I, with phosphorous oxychloride or thionyl chloride.

7. A process for the preparation of a compound of formula I.3, (I.3)

wherein $R^1$, $R^3$, $R^4$ and $R^5$ are as defined for compound of formula I, which comprises reacting a compound of formula II, (II)

wherein $R^1$, $R^3$, $R^4$ and $R^5$ are as defined for compound of formula I, with a hydrazine derivative.

8. A process for the preparation of a compound of formula II,

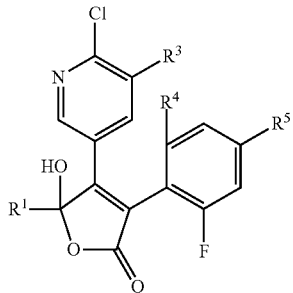
(II)

wherein $R^1$, $R^3$, $R^4$ and $R^5$ are as defined for compound of formula I, which comprises reacting a compound of formula III,

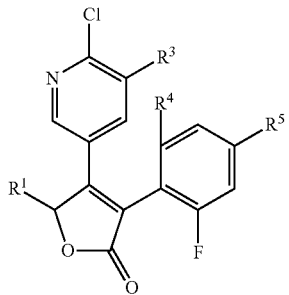
(III)

wherein $R^1$, $R^3$, $R^4$ and $R^5$ are as defined for compound of formula I, with oxygen, air, or 3-chloroperbenzoic acid.

9. A process for the preparation of a compound of formula III,

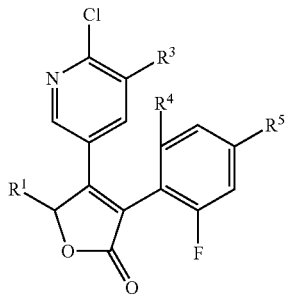
(III)

wherein $R^1$, $R^3$, $R^4$ and $R^5$ are as defined for compound of formula I, which comprises reacting a compound of formula IV,

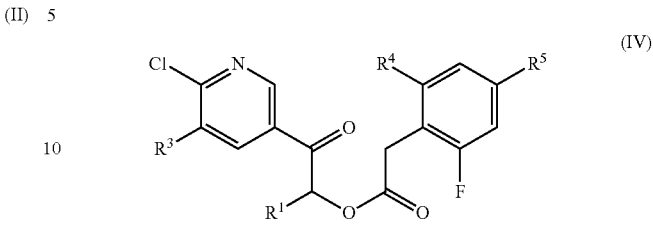
(IV)

wherein $R^1$, $R^3$, $R^4$ and $R^5$ are as defined for compound of formula I, with a base.

10. A fungicidal composition for controlling or protecting against phytopathogenic microorganisms, comprising as active ingredient at least one compound as defined in claim 1, in free form or in agrochemically usable salt form, and at least one adjuvant.

11. The composition according to claim 10 which comprises at least one additional fungicidally active compound, selected from the group consisting of azoles, pyrimidinyl carbinoles, 2-amino-pyrimidines, morpholines, anilinopyrimidines, pyrroles, phenylamides, benzimidazoles, dicarboximides, carboxamides, strobilurines, dithiocarbamates, N-halomethylthiotetrahydrophthalimides, copper-compounds, nitrophenols, organo-phosphorus-derivatives, pyridazines, triazolopyrimidines, carboxamides or benzamides.

12. A composition comprising at least one compound as defined in claim 1 and/or at least one pharmaceutically acceptable salt thereof, at least one pharmaceutically acceptable carrier and/or at least one pharmaceutically acceptable diluent.

13. A pharmaceutical composition comprising the compound as defined in claim 1 or a pharmaceutically acceptable salt thereof.

14. A pharmaceutical composition comprising 2% to 60%, by weight, of the compound as defined in claim 1 or a pharmaceutically acceptable salt thereof.

15. A method of controlling or preventing an infestation of crop plants, harvested food crops or non-living materials by phytopathogenic or spoilage microorganisms, which comprises the application of a compound as defined in claim 1, as active ingredient to the plant, to parts of the plants or to the locus thereof, to seeds or to any part of the non-living materials.

16. The method according to claim 15, wherein the phytopathogenic microorganisms are fungal organisms.

* * * * *